(12) United States Patent
Fleagle et al.

(10) Patent No.: US 6,631,817 B1
(45) Date of Patent: Oct. 14, 2003

(54) RE-CONFIGURABLE CRANE CARRIER

(75) Inventors: Jon E. Fleagle, Waynesboro, PA (US); Kurt W. Richter, Shippensburg, PA (US)

(73) Assignee: Grove U.S. LLC, Shady Grove, PA (US)

(*) Notice: Subject to any disclaimer, the term of this patent is extended or adjusted under 35 U.S.C. 154(b) by 89 days.

(21) Appl. No.: 09/666,599

(22) Filed: Sep. 20, 2000

(51) Int. Cl.[7] ............................................... B66C 23/78
(52) U.S. Cl. ..................................... 212/301; 212/302
(58) Field of Search ............................... 212/301, 302, 212/303, 304, 305, 306

(56) References Cited

U.S. PATENT DOCUMENTS

| | | |
|---|---|---|
| 2,518,410 A | 8/1950 | Willis |
| 3,184,076 A | 5/1965 | Brown et al. |
| 3,362,544 A | 1/1968 | Wellnitz |
| 3,578,352 A * | 5/1971 | Heine ...................... 280/43.23 |
| 3,747,957 A | 7/1973 | Noll |
| 3,836,012 A | 9/1974 | Grider et al. |
| 3,926,453 A * | 12/1975 | Leslie ...................... 280/81 R |
| 4,165,005 A | 8/1979 | Jokinen |
| 4,199,298 A | 4/1980 | Webre, Jr. et al. |
| 4,273,244 A | 6/1981 | Jensen et al. |
| 4,363,412 A | 12/1982 | Patel et al. |
| 4,434,994 A | 3/1984 | Pepin |
| 4,640,421 A | 2/1987 | Mason |
| 4,660,731 A | 4/1987 | Becker |
| 4,664,411 A | 5/1987 | Fix |
| 5,018,630 A * | 5/1991 | McGhie ...................... 212/233 |
| 5,029,895 A | 7/1991 | Anderson |
| 5,110,149 A | 5/1992 | Dahlstrom |
| 5,348,171 A | 9/1994 | Haman et al. |

FOREIGN PATENT DOCUMENTS

| | | | | |
|---|---|---|---|---|
| DE | 2837398 | * | 3/1980 | .................. 212/301 |
| JP | 55-106843 | * | 8/1980 | |
| JP | 59-109409 | * | 6/1984 | |

* cited by examiner

*Primary Examiner*—Thomas J. Brahan
(74) *Attorney, Agent, or Firm*—Birch, Stewart, Kolasch & Birch, LLP

(57) ABSTRACT

A mobile crane includes a chassis having first connection features located on a rear end thereof. An outrigger includes second connection features for mating with the first connection features. A tag axle assembly includes third connection features for mating with the first connection features. The first connection features may accept either the second connection features or the third connection features, so that the mobile crane may be selectively configured for highway travel and selectively configured for working operation. One or more axles of the mobile crane may be elevated when the tag axle assembly is connected to the first connection feature. Further, a wheeled boom dolly may be employed to share weight with the chassis when the mobile crane is travelling. By allowing the outrigger to be replaced with the tag axle assembly, the present invention allows the mobile crane to be conveniently configured for road travel in a manner suitable to the axle spacing and axle weight restrictions of the local area.

11 Claims, 5 Drawing Sheets

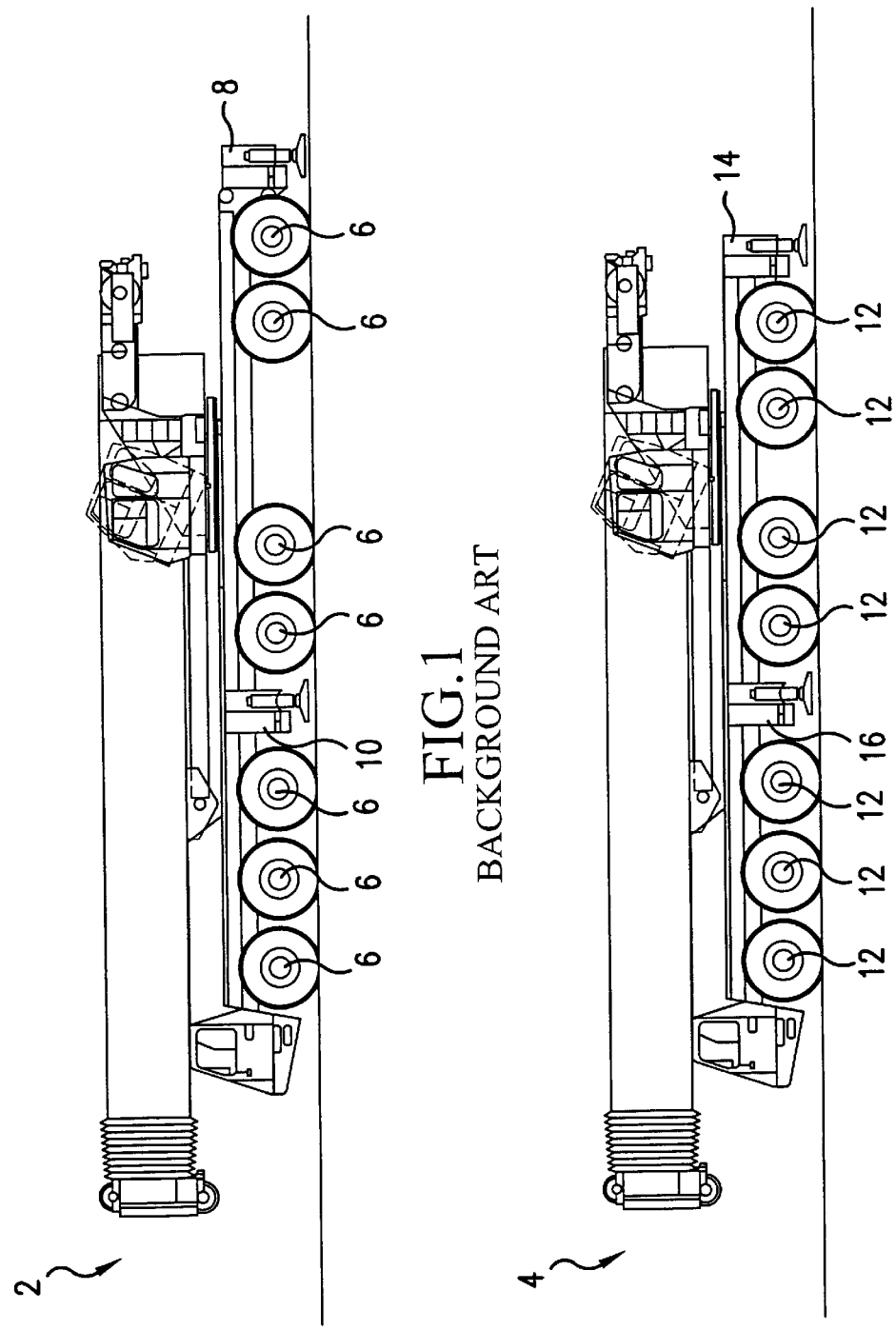

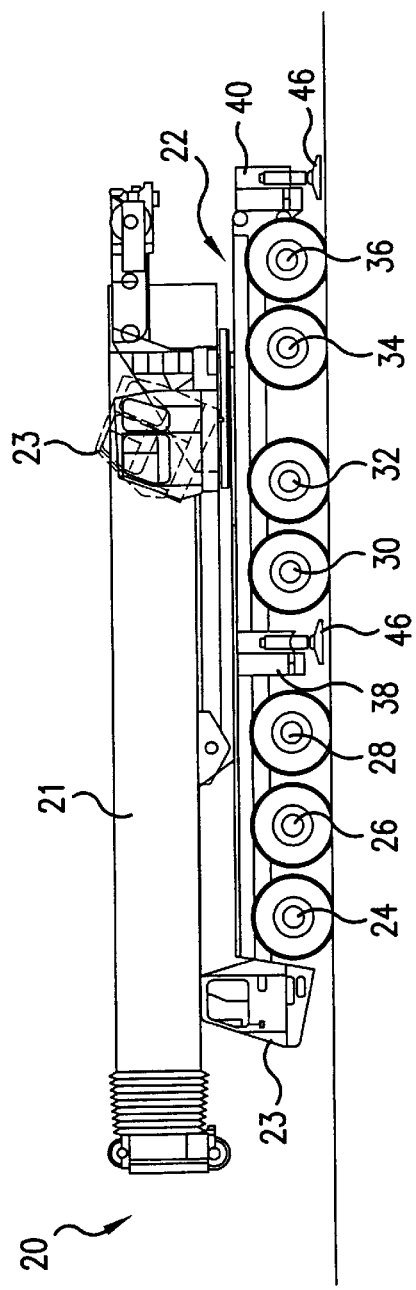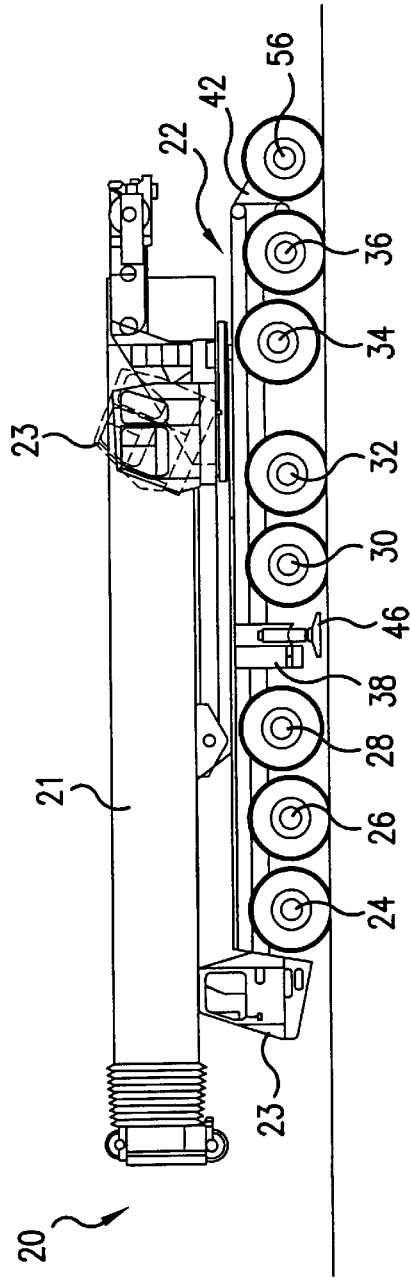

RE-CONFIGURABLE CRANE CARRIER

BACKGROUND OF THE INVENTION

1. Field of the Invention

The present invention relates to a mobile crane. More particularly, the present invention relates to a structural configuration of a mobile crane's chassis, a tag axle assembly, and an outrigger, which allows the mobile crane to be selectively variably configured for operation and selectively variably configured for road travel.

2. Description of the Relevant Art

In the past, a manufacturer of mobile cranes had to design at least two configurations of a mobile crane in order to better serve a world market. For example, FIG. 1 illustrates a mobile crane 2 designed taking into consideration certain factors pertinent to the United States market, whereas, FIG. 2 illustrates a mobile crane 4 designed for the European market.

The mobile crane 2 of FIG. 1 has a plurality of weight bearing axles 6, which are spaced relatively far apart, and a removable rear outrigger 8. Prior to travel on a U.S. road, the removable rear outrigger 8 is removed, and can be transported by a separate vehicle. Removing the rear outrigger 8 reduces the overall weight of the mobile crane 2. A middle outrigger 10 may be fixed, or removable, depending upon whether a further weight reduction is required in order to meet maximum weight restrictions for road travel.

The axles 6 are spaced relatively far apart in order to meet axle spacing requirements set by federal, state or local bridge weight regulations. For example, the minimum wheel spacing requirement in some areas is 18 feet, measured from the first axle in the first axle group to the first axle in the second axle group.

The mobile crane 2 is particularly well suited for the U.S. market because it can be driven to and from most job sites without requiring special permits or waivers of the maximum weight or minimum axle spacing requirements for road travel. The larger spacing between axles 6 and the larger overall length of the mobile crane 2, while enabling the mobile crane 2 to meet road travel restrictions, somewhat limit the maneuverability of the mobile crane 2 on narrow and/or curvy roads. However, because U.S. roads are typically designed with minimal curvatures and are usually relatively wide, the larger axle spacing and overall length still allows the mobile crane 2 to be safely driven to job sites.

The mobile crane 4 of FIG. 2 has a plurality of weight bearing axles 12, which are spaced relatively close, and a fixed rear outrigger 14 and fixed middle outrigger 16. The other structural features of the mobile crane 4 are similar or identical to the other structural features of the mobile crane 2.

The mobile crane 4 is particularly well suited for the European market. European roads are often narrow with tight curves. Therefore, closer axle spacing and a shorter overall length is desired in order to maneuver the mobile crane 4 to and from a job site. There are usually no axle spacing requirements for bridge travel, which facilitates shorter overall lengths. Further, in European countries, the maximum axle weight requirements are usually set much higher than the U.S. requirements. For example, mobile cranes driven in Europe typically have axle weights up to 12 metric tons. This often makes it more feasible to have fixed outriggers on the crane chassis. Of course, the rear outrigger 14 or middle outrigger 16 could be removable if needed, in order to meet the European maximum axle weight requirements.

When a manufacturer of mobile cranes attempts to design a new mobile crane for the world market, a problem arises. If the crane manufacturer offers a mobile crane with a U.S. oriented carrier or chassis, sales of the mobile crane in Europe will suffer due to poor mobility on European roads. If the crane manufacturer offers a mobile crane with a European oriented carrier or chassis, sales in the U.S. will suffer due to a frequent need to obtain special permits and waivers in order to drive the mobile crane on U.S. roads. Therefore, it has been necessary for a worldwide crane manufacturer to undertake the costly and time consuming task of designing, testing and building two different crane carriers for a single crane model, one chassis for the U.S. market and one chassis for the European market.

SUMMARY OF THE INVENTION

It is an object of the present invention to eliminate the cost and time required in designing, testing and/or building two carriers or chassises for a single crane design, while still providing a crane to serve a worldwide market.

It is an object of the present invention to provide a chassis structure which can be easily converted or reconfigured for use in the U.S. market, European market, or other markets.

These and other objects are accomplished by a mobile crane assembly comprising: a chassis; first connection features located on a portion of said chassis; an outrigger including at least one ground engaging portion for engaging the ground when said mobile crane is stationary; second connection features located on said outrigger for mating with said first connection features of said chassis to removably attach said outrigger to said portion of said chassis; a tag axle assembly including at least one wheel for rolling along a ground surface; and third connection features located on said tag axle assembly for mating with said first connection features of said chassis to removably attach said tag axle assembly to said portion of said chassis, wherein said first connection features may accept either said second connection features or said third connection features, such that said mobile crane can be connected to either said outrigger or said tag axle assembly, respectively.

Further, these and other objects are accomplished by a method of operating a mobile crane comprising the steps of providing a mobile crane including a chassis with first connection features located on a portion of the chassis; an outrigger having second connection features being attached to said first connection features; and a tag axle assembly having third connection features; detaching the second connection features from the first connection features to remove the outrigger from the portion of the chassis; attaching the third connection features to the first connection features to attach the tag axle assembly to the portion of the chassis; engaging at least two wheels of the tag axle assembly with a ground surface; and moving the mobile crane.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 1 is a side view of a mobile crane having a chassis built for travel on typical U.S. roads in accordance with the background art;

FIG. 2 is a side view of a mobile crane having a chassis built for travel on typical European roads in accordance with the background art;

FIG. 3 is a side view of a mobile crane having a chassis, in accordance with the present invention, with the chassis configured for European travel;

FIG. 4 is a side view of the mobile crane of FIG. 3 having the chassis configured for U.S. travel;

DETAILED DESCRIPTION OF THE INVENTION

Figure 5:
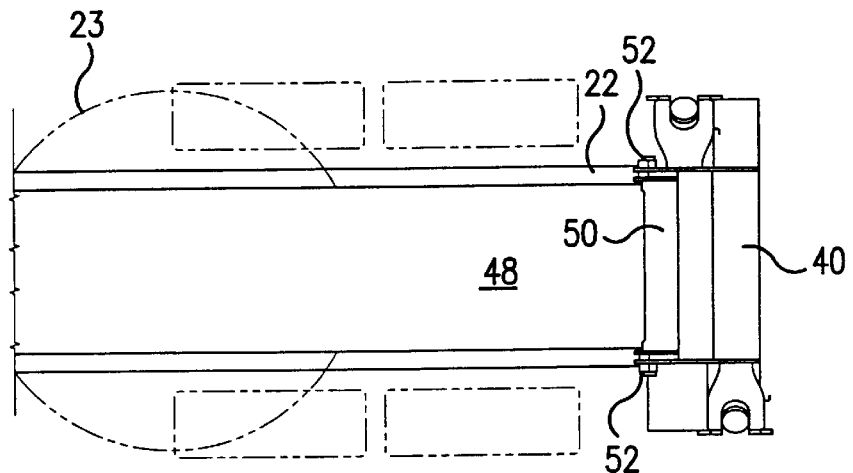
FIG. 5 is a top view of a removable outrigger attached to the chassis of FIG. 3.

FIG. 3 illustrates one embodiment of a mobile crane 20, in accordance with the present invention. The mobile crane 20 includes a telescopic boom 21 and may include one or more drive/operation cabins 23. The mobile crane 20 features a re-configurable chassis 22. FIG. 3 illustrates the chassis 22 configured for European road travel.

The chassis 22 includes a first axle 24, a second axle 26, a third axle 28, a fourth axle 30, a fifth axle 32, a sixth axle 34, a seventh axle 36, a fixed middle outrigger 38, and a removable rear outrigger 40. The middle outrigger 38 could also be removable, if desired.

When the mobile crane 20 is operated on European roads, the middle and rear outriggers 38, 40 can remain attached to the chassis 22, assuming that the weight restrictions of the European roads are complied with. If the weight restrictions are a concern, one or both of the middle and rear outriggers 38, 40 may be removed, and transported separately. Further, when the mobile crane 20 is operated on European roads, all of the axles 24, 26, 28, 30, 32, 34, 36 are weight bearing, since the axle spacing for bridge travel is not a concern.

Figure 7:
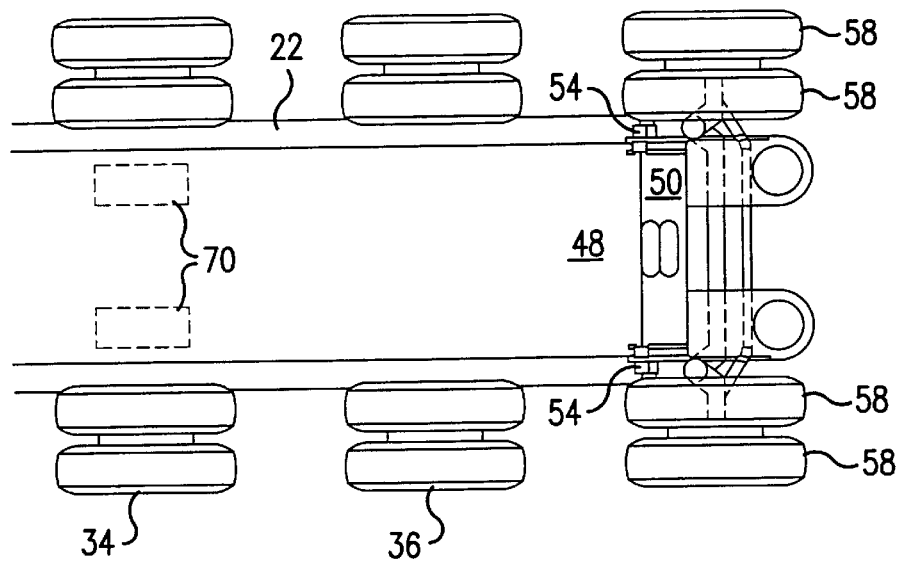
FIG. 7 is a top view of a removable tag axle assembly attached to the chassis of FIG. 3.
Figure 8:
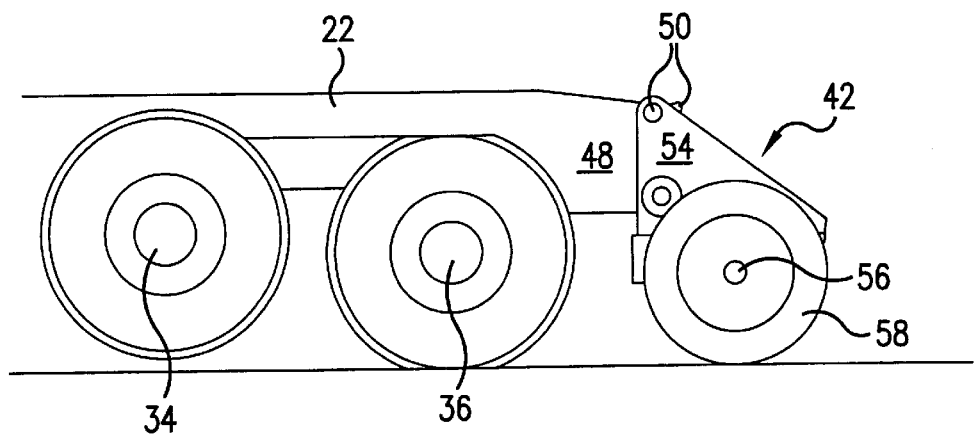
FIG. 8 is a side view of the removable tag axle assembly of FIG. 7.

FIG. 4 illustrates the mobile crane 20 with its chassis 22 configured for U.S. road travel. The third axle 28 and the sixth axle 34 have been raised, so that they are no longer load bearing. As illustrated in FIGS. 7 and 8, the third and sixth axles 28, 34 may be raised by any known suitable mechanism, such as the Megatrak™ suspension system, wherein an hydraulic cylinder with an accumulator 70 acts as a spring. Further, the third and sixth axles 28, 34 may be either steerable or fixed when load bearing.

As illustrated in FIG. 4, the removable rear outrigger 40 of chassis 22 has been removed and replaced with a tag axle assembly 42. Of course, the middle outrigger 38 could also be removed to further reduce the overall weight of the mobile crane 20. By raising the third and sixth axles 28, 34, and by replacing the rear outrigger 40 with the tag axle assembly 42, the mobile crane 20 can be made to meet the maximum weight restriction for U.S. road travel as well as the axle spacing requirements set by federal, state or local bridge weight regulations.

Figure 6:
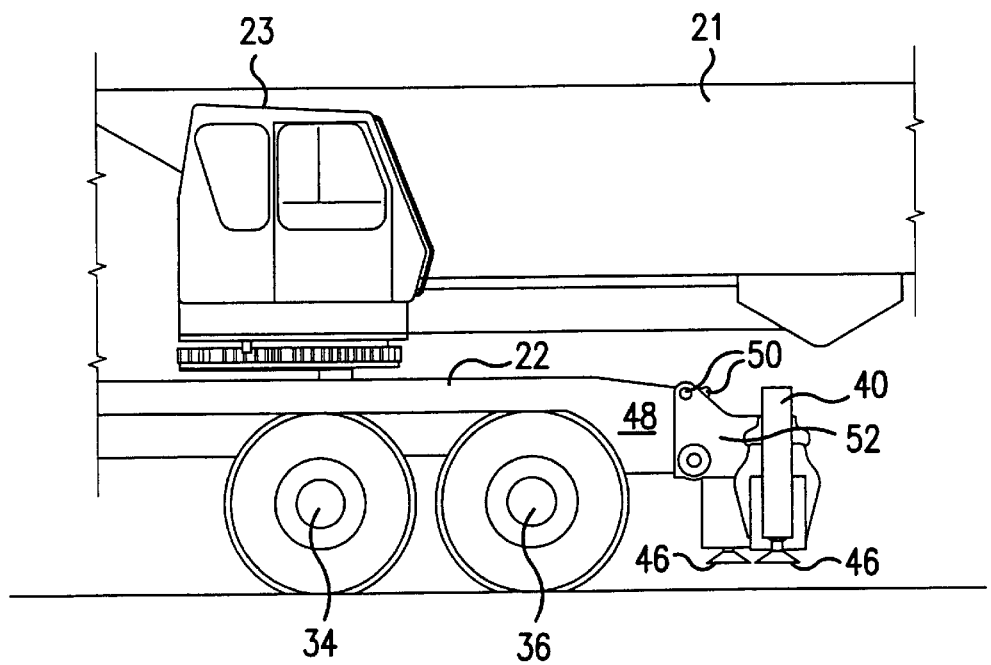
FIG. 6 is a side view of the removable outrigger of FIG. 5.

FIGS. 5 and 6 are more detailed top and side view illustrations of the removable rear outrigger 40 attached to a rear end portion 48 of the chassis 22. The rear end portion 48 includes first connection features 50. The rear outrigger 40 includes second connection features 52 for mating with the first connection features 50. The rear outrigger 40 also includes two ground engaging portions 46. The boom 21 may be used to lift and install/remove the rear outrigger 40.

FIGS. 7 and 8 are top and side view illustrations of the removable tag axle assembly 42 attached to the rear end portion 48 of the chassis 22. The tag axle assembly 42 includes third connection features 54 for mating with the first connection features 50. The third connection features 54 would be similar or identical to the second connection features 52 of the outrigger 40. The tag axle assembly 42 also includes a load bearing axle 56 supporting two or more wheels 58. Preferably, the tag axle assembly 42 includes suspension members, and the wheels 58 are non-steerable, steerable, or self-steering, as desired. The boom 21 may be used to lift and install/remove the tag axle assembly 42.

The first, second and third connection features 50, 52, 54 are constructed in accordance with presently available and employed connection features used in conjunction with known removable tag axle assemblies or known removable outriggers. Therefore, the details of the connection features are not particular to the present invention. The present invention may be used in combination with any connection features, known or later invented, so long as the second and third connection features 52, 54 will mate with the first connection features 50, and provide sufficient stability to the tag axle assembly 42 and rear outrigger 40.

The tag axle assembly 42 may include more than one axle. Such a multiaxle arrangement may be advantageous in further reducing the axle weights. Again, one or more of the axles of the tag axle assembly 42 may be non-steerable, steerable, or self-steering, as desired.

It should also be noted that the rear outrigger 40 may be removed and the tag axle assembly 42 installed even when the crane 20 is used in Europe, even though local regulation would not require the configuration. The operator/driver might desire this option, especially when the mobile crane 20 is being moved to a job site across European roads which are relatively wide and straight.

Figure 9:
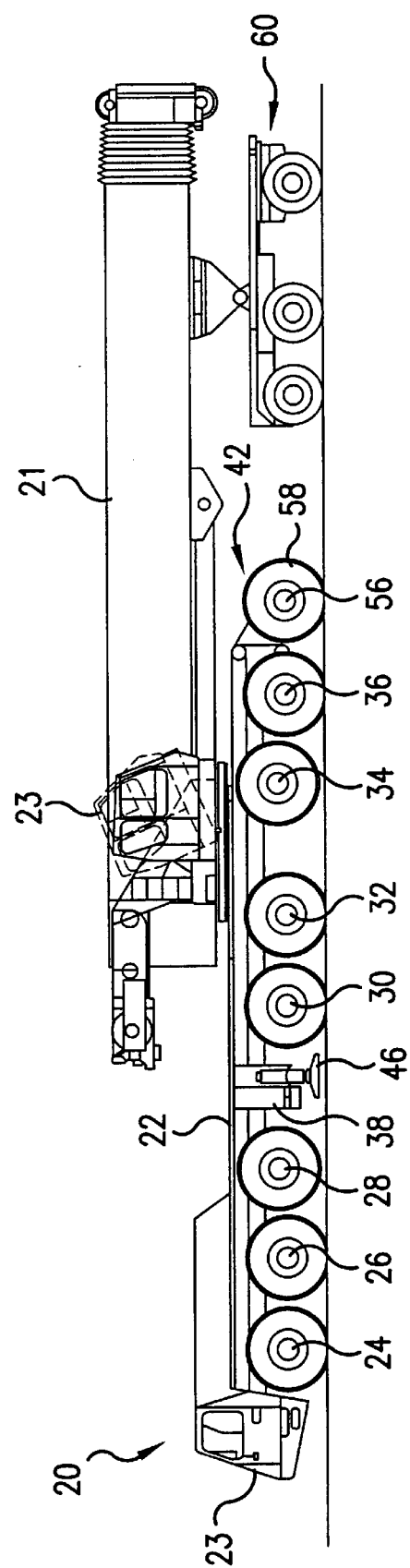
FIG. 9 is a side view of the mobile crane of FIG. 4 with a wheeled boom dolly.

FIG. 9 illustrates a configuration of the mobile crane similar to FIG. 4 except that the boom 21 is rotated to extend over the rear end portion 48 of the chassis 22, and is attached to and supported by a trailing, wheeled boom dolly 60. This configuration spreads the weight of the mobile crane 20 over more axles, thus reducing the load per axle even more than the configuration of FIG. 4. Moreover, the spacing of the axle groups, including the axles of the wheeled boom dolly 60, still meets the spacing requirements of the United States bridge weight regulations.

As illustrated in the above embodiment, replacing the removable rear outrigger 40 with the removable tag axle assembly 42 allows a compact crane chassis 22, designed for narrow curvy roads, such as in Europe, to be easily re-configured. For example, the chassis 22 can be re-configured for road travel in areas where the horizontal distance between axle groups needs to be increased in order to meet government regulations for traveling on roads or bridges, such as in the United States. The suspension system, type of steering and the wheel arrangement for the tag axle assembly may all be modified so that the chassis 22 can be made to meet the regulatory requirements of the area of the world where the mobile crane 20 will be used.

The above disclosure and drawings have illustrated an easily re-configurable mobile crane 20 having seven axles, such as for a 500 short ton crane. The concepts of the present invention can be applied to any crane's carrier, regardless of the number of axles. For example, the crane could have fewer or more than seven axles, and axles other than the third and sixth axles could be raised to alter the configuration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A mobile crane assembly comprising:
    a chassis;
    first connection features located on a portion of said chassis;
    an outrigger assembly including at least two ground engaging outriggers for engaging the ground when said mobile crane is stationary;
    second connection features located on said outrigger assembly for mating with said first connection features of said chassis to removably attach said outrigger assembly to said portion of said chassis;
    a tag axle assembly including at least two wheels for rolling along a ground surface, while said mobile crane is driven along a road; and
    third connection features located on said tag axle assembly for mating with said first connection features of said chassis to removably attach said tag axle assembly to said portion of said chassis, wherein said first connection features may alternatively accept one of said second connection features or said third connection features, such that said mobile crane can be connected to one of said outrigger assembly or said tag axle assembly, respectively.

2. The mobile crane assembly according to claim 1, wherein said portion of said chassis is a rear end portion, taken in a direction of normal travel of said mobile crane.

3. The mobile crane assembly according to claim 1, wherein said tag axle assembly is steerable.

4. The mobile crane assembly according to claim 1, wherein said tag axle assembly includes two axles and at least four wheels.

5. The mobile crane assembly according to claim 1, further comprising:
    a boom attached to said chassis; and
    a wheeled boom dolly for supporting said boom for travel.

6. The mobile crane assembly according to claim 5, wherein said wheeled boom dolly is removably attached to said boom and separate from said chassis.

7. The mobile crane assembly according to claim 1, wherein said chassis includes a plurality of axles, each of which supports a plurality of wheels.

8. The mobile crane assembly according to claim 7, means associated with at least one axle of said plurality of axles for selectively elevating said at least one axle so that the plurality of wheels associated with said at least one axle are elevated above the ground surface, while said mobile crane is driven along a road.

9. The mobile crane assembly according to claim 8, wherein said portion of said chassis is a rear end portion taken in a direction of normal travel for said mobile crane.

10. The mobile crane assembly according to claim 9, wherein said tag axle assembly includes one axle and at least two wheels.

11. The mobile crane assembly according to claim 10, further comprising:
    a boom attached to said chassis; and
    a wheeled boom dolly for supporting said boom for travel wherein said wheeled boom dolly is removably attached to said boom and separate from said chassis.

* * * * *